United States Patent
McDonnall et al.

(10) Patent No.: US 10,729,564 B2
(45) Date of Patent: Aug. 4, 2020

(54) SENSOR SYSTEM

(71) Applicant: Ripple, LLC, Salt Lake City, UT (US)

(72) Inventors: Daniel Allen McDonnall, Salt Lake City, UT (US); Scott Darold Hiatt, South Jordan, UT (US); Brian Scott Crofts, Salt Lake City, UT (US); Christopher Farand Smith, North Salt Lake, UT (US); Andrew Miller Wilder, Salt Lake City, UT (US)

(73) Assignee: Ripple LLC, Salt Lake City, UT (US)

( * ) Notice: Subject to any disclaimer, the term of this patent is extended or adjusted under 35 U.S.C. 154(b) by 103 days.

(21) Appl. No.: 15/870,362

(22) Filed: Jan. 12, 2018

(65) Prior Publication Data
US 2019/0216619 A1     Jul. 18, 2019

(51) Int. Cl.
*A61F 2/72*     (2006.01)
*A61B 5/0488*     (2006.01)
(Continued)

(52) U.S. Cl.
CPC .............. *A61F 2/72* (2013.01); *A61B 5/0017* (2013.01); *A61B 5/0492* (2013.01);
(Continued)

(58) Field of Classification Search
CPC ...... A61F 2/72; A61F 2/70; A61F 2/68; A61F 2002/705; A61F 2002/701; B25J 19/0025;
(Continued)

(56) References Cited

U.S. PATENT DOCUMENTS

| | | |
|---|---|---|
| 4,566,464 A | 1/1986 | Piccone et al. |
| 4,735,208 A | 4/1988 | Wyler et al. |

(Continued)

FOREIGN PATENT DOCUMENTS

WO     WO 2019/199364     10/2018

OTHER PUBLICATIONS

U.S. Appl. No. 14/729,027, Non-Final Office Action dated Jul. 13, 2017.
(Continued)

*Primary Examiner* — Suba Ganesan
*Assistant Examiner* — Aren Patel
(74) *Attorney, Agent, or Firm* — Phillips Winchester; Jared L. Cherry

(57) ABSTRACT

Disclosed herein are systems and methods for sensor systems. In one embodiment, a system may include an implantable component and an external component. The implantable component may comprise a housing and an electrode array configured to receive a plurality of biopotential signals. The housing may comprise a wireless power receiver and a wireless data transmitter to transmit representations of the biopotential signals. The external component may comprise a wireless data receiver configured to receive the plurality of digital representations of the biopotential signals and a wireless power transmitter configured to provide power to the internal component. A shielding component may separate the wireless power transmitter from the wireless data receiver. An interface may be configured to communicate with a prosthesis and configured to cause the prosthesis to implement a voluntary motion based on the plurality of digital presentations of the biopotential signals.

18 Claims, 5 Drawing Sheets

(51) Int. Cl.
*A61B 5/00* (2006.01)
*A61B 5/0492* (2006.01)
*A61F 2/70* (2006.01)

(52) U.S. Cl.
CPC .. *A61B 5/04888* (2013.01); *A61B 2560/0214* (2013.01); *A61F 2002/705* (2013.01)

(58) Field of Classification Search
CPC .. B25J 19/0045; A61B 5/0017; A61B 5/0031; A61B 5/04851; A61B 5/4888; A61B 5/0492; A61B 5/6811
USPC .............. 623/25, 27, 47, 53; 608/33
See application file for complete search history.

(56) References Cited

U.S. PATENT DOCUMENTS

| | | | |
|---|---|---|---|
| 4,850,359 A | 7/1989 | Putz | |
| 4,903,702 A | 2/1990 | Putz | |
| 5,097,835 A | 3/1992 | Putz | |
| 5,279,305 A | 1/1994 | Zimmerman et al. | |
| 5,400,782 A | 3/1995 | Beaubiah | |
| 5,433,742 A | 7/1995 | Willis | |
| 5,456,254 A | 10/1995 | Pietroski et al. | |
| 5,520,180 A | 5/1996 | Uy et al. | |
| 5,681,514 A | 10/1997 | Woody | |
| 5,707,367 A | 1/1998 | Nilsson | |
| 5,843,155 A | 12/1998 | Axelgaard | |
| 5,868,136 A | 2/1999 | Fox et al. | |
| 5,895,369 A | 4/1999 | Flower | |
| 5,904,712 A | 5/1999 | Axelgaard | |
| 5,924,983 A | 7/1999 | Takaki et al. | |
| 6,024,702 A | 2/2000 | Iversen | |
| 6,091,979 A | 7/2000 | Madsen | |
| 6,095,148 A | 8/2000 | Shastri | |
| 6,251,978 B1 | 6/2001 | McCullough | |
| 6,259,937 B1 | 7/2001 | Schulman et al. | |
| 6,304,784 B1 | 10/2001 | Allee et al. | |
| 6,480,743 B1 | 11/2002 | Kirkpatrick et al. | |
| 6,529,774 B1 | 3/2003 | Greene | |
| 6,624,510 B1 | 9/2003 | Chan et al. | |
| 6,636,769 B2 * | 10/2003 | Govari ................. | A61B 5/0031 128/903 |
| 6,643,552 B2 | 11/2003 | Edell et al. | |
| 6,696,575 B2 | 2/2004 | Schmidt et al. | |
| 6,792,314 B2 | 9/2004 | Byers et al. | |
| 6,813,475 B1 * | 11/2004 | Worthy ................. | H04B 7/084 455/2.01 |
| 6,829,498 B2 | 12/2004 | Rousche et al. | |
| 6,862,479 B1 | 3/2005 | Whitehurst et al. | |
| 6,907,299 B2 | 6/2005 | Han | |
| 6,973,342 B1 | 12/2005 | Swanson | |
| 6,993,392 B2 | 1/2006 | Nicolelis et al. | |
| 7,006,859 B1 | 2/2006 | Osorio et al. | |
| 7,027,874 B1 | 4/2006 | Sawan et al. | |
| 7,107,097 B2 | 9/2006 | Stern et al. | |
| 7,162,308 B2 | 1/2007 | O'Brien et al. | |
| 7,190,989 B1 | 3/2007 | Swanson et al. | |
| 7,212,851 B2 | 5/2007 | Donoghue et al. | |
| 7,229,437 B2 | 6/2007 | Johnson et al. | |
| 7,231,259 B2 | 6/2007 | Jenney et al. | |
| 7,234,225 B2 | 6/2007 | Johnson et al. | |
| 7,236,834 B2 | 6/2007 | Christopherson et al. | |
| 7,264,876 B2 | 9/2007 | Smalley et al. | |
| 7,272,427 B2 | 9/2007 | Ristolainen | |
| 7,330,756 B2 | 2/2008 | Marnfeldt | |
| 7,337,012 B2 | 2/2008 | Maghribi et al. | |
| 7,346,391 B1 | 3/2008 | Osorio et al. | |
| 7,347,826 B1 | 3/2008 | Karicheria et al. | |
| 8,032,210 B2 * | 10/2011 | Finneran .............. | A61B 5/0492 600/546 |
| 8,467,844 B2 | 6/2013 | Rea et al. | |
| 8,799,562 B2 * | 8/2014 | Kawamura .......... | G06F 3/0608 707/692 |
| 8,832,585 B2 * | 9/2014 | Missig ................ | G06F 3/04883 715/778 |
| 9,037,434 B2 * | 5/2015 | Willett, Jr. ............. | F01D 11/14 702/155 |
| 9,061,134 B2 * | 6/2015 | Askin, III ............ | A61B 5/0408 |
| 9,962,085 B2 * | 5/2018 | Griffith ................. | H02J 7/025 |
| 2003/0228748 A1 | 12/2003 | Nelson | |
| 2004/0243204 A1 | 12/2004 | Maghribi et al. | |
| 2005/0143790 A1 | 6/2005 | Kipke et al. | |
| 2005/0182423 A1 | 8/2005 | Schulte et al. | |
| 2005/0192644 A1 | 9/2005 | Boveja et al. | |
| 2006/0058627 A1 | 3/2006 | Flaherty et al. | |
| 2006/0129056 A1 | 6/2006 | Leuthardt et al. | |
| 2006/0149319 A1 | 7/2006 | Kuo et al. | |
| 2006/0224060 A1 | 10/2006 | Garell et al. | |
| 2006/0264729 A1 | 11/2006 | Putz et al. | |
| 2007/0123963 A1 | 5/2007 | Krulevitch | |
| 2007/0167815 A1 | 7/2007 | Jacobsen et al. | |
| 2008/0058875 A1 | 3/2008 | Greenberg et al. | |
| 2008/0319292 A1 | 12/2008 | Say et al. | |
| 2009/0149913 A1 | 6/2009 | Putz et al. | |
| 2009/0254134 A1 | 10/2009 | Nikolov et al. | |
| 2010/0268055 A1 | 10/2010 | Jung | |
| 2013/0274574 A1 | 10/2013 | Say | |
| 2013/0338746 A1 * | 12/2013 | Guvanasen .......... | A61N 1/0502 607/116 |
| 2016/0043571 A1 * | 2/2016 | Kesler .................. | H02J 50/12 307/104 |
| 2016/0302686 A1 * | 10/2016 | Einarsson ............. | A61F 2/60 |
| 2018/0256030 A1 * | 9/2018 | Lee ...................... | A61B 5/0031 |

OTHER PUBLICATIONS

U.S. Appl. No. 14/729,027, Final Office Action dated Mar. 9, 2018.
U.S. Appl. No. 12/889,310, Non-Final Office Action dated Aug. 14, 2014.
U.S. Appl. No. 12/889,310, Non-Final Office Action dated Jan. 9, 2013.
U.S. Appl. No. 12/889,310, Final Office Action dated May 10, 2013.
International Application No. PCT/US2019/013157; Written Opinion dated Sep. 10, 2019; 3 p.
International Application No. PCT/US2019/013157; International Search Report dated Sep. 10, 2019; 3 p.

* cited by examiner

SENSOR SYSTEM

FEDERALLY SPONSORED RESEARCH OR DEVELOPMENT

This invention was made with U.S. Government support under one or more of contract nos. W911NF-17-C-0058, W911NF-15-C-0014, HR0011512791 awarded by Defense Advanced Research Projects Agency and NS067784-01A1 awarded by the National Institutes of Health. The U.S. Government may have certain rights in this invention.

TECHNICAL FIELD

This disclosure relates to systems and methods for obtaining biopotential signals from a plurality of electrodes in communication with existing muscles or nerves of a patient. More particularly, but not exclusively, such systems may be used to control external devices, such as a prosthesis.

DETAILED DESCRIPTION OF PREFERRED EMBODIMENTS

Figure 1:
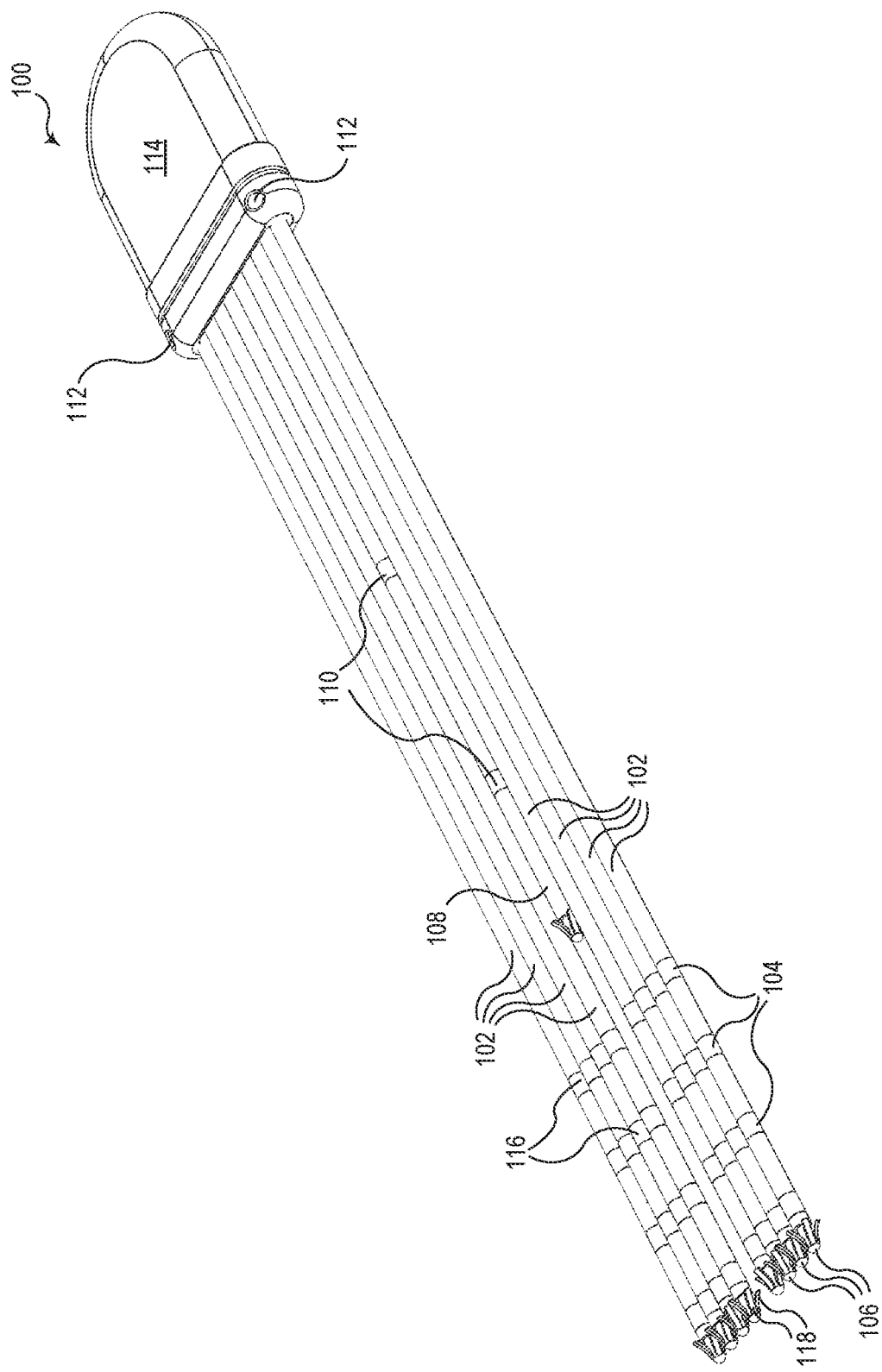
FIG. 1 illustrates one embodiment of an implantable component of a myoelectric sensor system having a plurality of leads and a plurality of electrodes disposed on each lead consistent with embodiments of the present disclosure.

Disclosed herein are systems and methods for an implantable myoelectric sensor system that may be utilized in a variety of applications. In some embodiments consistent with the present disclosure, the systems and methods disclosed herein may be utilized to control prosthetic devices. A prosthetic device may be controlled using existing muscle groups in the residual limb that the user may be able to voluntarily activate. By connecting sensors to these muscles, the patient may be able to control the prosthetic device by activating the remaining muscles. The sensors may be connected to amplification and acquisition circuitry and a processor to control movement in a prosthetic device. As used in the present disclosure, the term myoelectric prosthesis refers to devices that use biopotential signals or potentials from voluntarily activated muscles to control the movements of a prosthesis.

In connection with a myoelectric prosthesis, biopotential signals may be collected via an electrode, lead, or sensor. Leads are structures that contain one or more electrodes or sensors that are individually placed, or placed in conjunction with other leads. Biopotential channels are electrical differences recorded between one or more electrodes. Electrodes/leads/sensors may be placed on or near the surface of the muscle or implanted into the muscle. A biopotential-signal-receiving device may also be implanted and may connect with an external transceiver via a wireless communication channel.

According to various embodiments, systems and methods consistent with the present disclosure may include a wireless multichannel myoelectric implant. In some embodiments, a wireless multichannel implant may be used to acquire biopotential signals from implanted electrodes. Representations of the acquired biopotential signals may be transmitted wirelessly to a system outside the body configured to receive, processes, and utilize the signals to control a myoelectric prosthesis.

It may be difficult during a surgery to implant an electrode to determine whether the electrode receives a specific biopotential signal. Accordingly, in various embodiments consistent with the present disclosure, an array of electrodes may be implanted on a plurality of leads to ensure broad coverage of the muscles in the implant area. Signals from the array of electrodes may be analyzed following implantation and processed to make one or more "virtual pairs" of electrodes, which may be selected for use in controlling a prosthesis. In other words, the array of electrodes may be utilized in a flexible configuration that allows for selection of one or more "virtual pairs" that best correspond to a desired biopotential signal used to control a prosthesis.

The embodiments of the disclosure will be best understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

FIG. 1 illustrates one embodiment of an implantable component 100 of a myoelectric sensor system having a plurality of leads 102 and a plurality of electrodes 104 disposed on each lead consistent with embodiments of the present disclosure. The plurality of leads 102 may each connect to a hermetic feedthrough on a housing 114. In various embodiments, the housing 114 may be formed of a bio-compatible material and may be hermetically sealed to allow for implantation in a patient. In one specific embodiment, the housing 114 may be formed of ceramic. A plurality of suture holes 112 may be disposed on the housing 114 and may allow the housing to be secured to adjacent tissue. As discussed in greater detail below, the housing 114 may comprise electronics to receive signals from the plurality of electrodes 104 and to communicate with an associated device.

The plurality of leads 102 may be flexible, and may be independently positioned within one or more muscle groups. The leads may be wire, helically wound wire or of other constructions including a biostable polymer comprising a plurality of distinct conductive particles. In the illustrated embodiment, implantable component 100 includes eight full length leads 102, each of which includes four electrodes 104.

A reference lead 108 may include a plurality of reference electrodes 110. A reference electrode 110 may provide a stable electrical potential against which the electrical potential of other electrodes 104 may be amplified and acquired. The system may be referred to as a "single-ended" reference. The "single-ended" reference may allow for the generation of "virtual pairs" in digital signal processing, rather than using analog amplifiers.

In addition to creating differential pairs between reference electrodes 110 and electrodes 104, "virtual pairs" of electrodes may also be generated after acquisition by a comparison the signal from any electrodes 104 to the signal from any other electrode. For example, a "virtual pair" may be created by comparison of the signals received by the two electrodes identified by reference number 116. In other words, a "virtual pair" may be generated as a difference between one of the plurality of electrodes and any other of the plurality of electrodes. A "virtual pair" may be generated from multiple signals from electrodes located on one lead or on separate leads. The ability to create a "virtual pair" based on two or more electrode signals provides a wide array of possible combinations. The large number of possible combinations may be analyzed to identify the specific combinations to achieve a specific result (e.g., utilization of a muscle group to control a prosthesis).

An anchor 106 may be disposed at the end of each lead 102 and reference lead 108. The anchors may be configured to hold the leads 102, 108 in place. In the illustrated embodiment, a plurality of flanges 118 may oppose motion in the direction of the housing 114. In contrast, when the leads 102, 108 are inserted, the flanges may be pressed inward and offer little resistance.

Figure 2A:
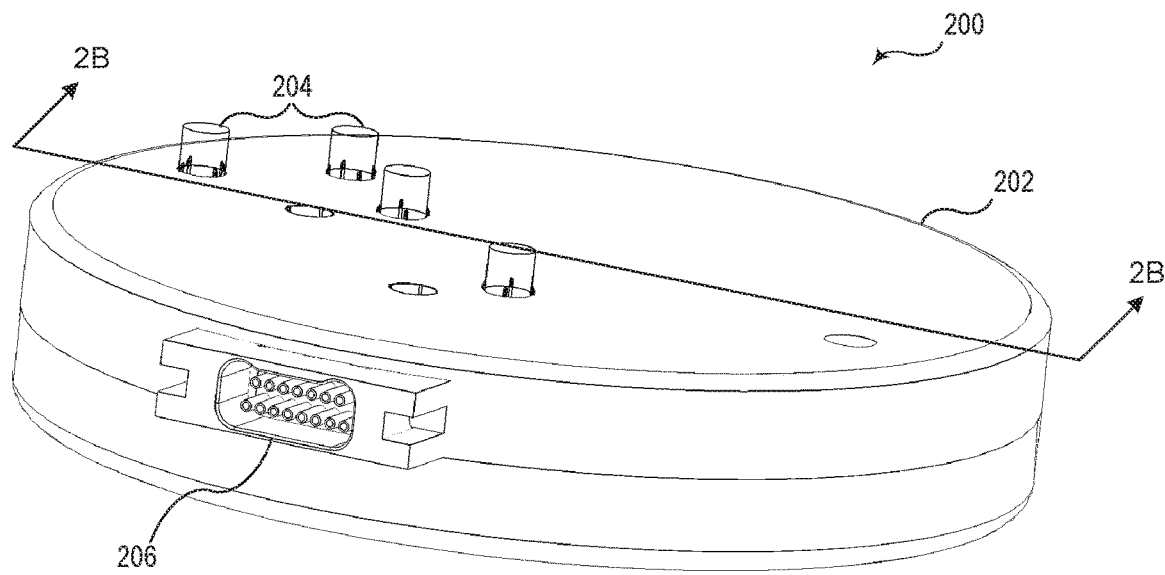
FIG. 2A illustrates a perspective view of an external transceiver assembly configured to power and communicate with an implantable electrode consistent with embodiments of the present disclosure.

FIG. 2A illustrates a perspective view of an external transceiver assembly 200 configured to power and communicate with an implantable electronics package consistent with embodiments of the present disclosure. In various embodiments, external transceiver assembly 200 may be used with implantable component 100 illustrated in FIG. 1. The external transceiver assembly may be positioned above the implantable component, and in some embodiments, may be housed within a prosthesis controlled by using biopotential signals received from the implantable component.

External transceiver assembly 200 may comprise a housing 202 configured to contain electronics for communicating with an implantable component. A connector 206 may provide an interface for controlling a prosthesis or other device. Power may also be provided via connector 206 for both the external transceiver assembly 200 and an associated implanted component. A plurality of light sources 204 may be disposed on the surface of external transceiver assembly 200. The plurality of light sources 204 may provide information regarding the status of the external transceiver assembly 200 and/or an associated implantable component. In some embodiments, the external transceiver may include switched or buttons to control operation on the device, including turning off power to the implanted device, changing decode processing parameters such as gain, or switching processing algorithms. In some embodiments, the plurality of light sources 204 may be used in connection with a corresponding plurality of buttons that may be used to provide input to the external transceiver assembly 200.

The external transceiver may have a tunable element, such as a trimmable capacitor, to optimize the power transfer efficiency for individual implants or relative placement of the external transceiver and implanted device.

Figure 2B:
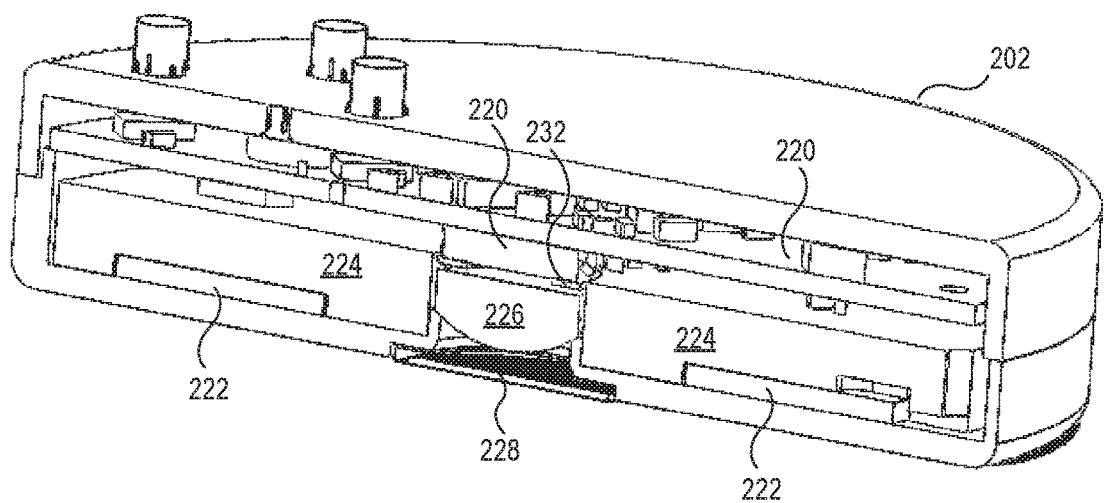
FIG. 2B illustrates a cross-sectional view of the external transceiver assembly of FIG. 2A taken along line 2B-2B consistent with embodiments of the present disclosure.

FIG. 2B illustrates a cross-sectional view of the external transceiver assembly 200 of FIG. 2A taken along line 2B-2B consistent with embodiments of the present disclosure. Housing 202 includes a printed circuit board (PCB) 220 to which a plurality of electronics may be mounted. The electronics may be configured to enable communication with an implantable component via a receiver 228. In some embodiments, the receiver may comprise an infrared receiver. The electronics may have components to communicate to the implant by means of amplitude modulation of the inductive powering signal.

Communication from an implantable component may be performed with a receiver 228. In some embodiments, the receiver 228 may comprise an infrared receiver. The infrared frequency range may be well suited to transcutaneous transmission; however, the transceiver may operate using other frequencies in the electromagnetic spectrum. A lens 226 may be configured to focus electromagnetic energy received from an implantable component to the receiver 228. A lens cover 230 may be disposed at the opening of an aperture in which the lens 226 and receiver 228 are disposed. A second electromagnetic shield 234 may be disposed over the receiver to shield the receiver from noise from the power transmitter. In some embodiments, the second electromagnetic shield 234 may be formed of metal.

An inductive coil 222 may be disposed about a portion of the outer surface of housing 202 nearest to the implantable component. The inductive coil 222 may be configured to wirelessly provide electrical power to the implantable component. The inductive coil 222 may be inductively coupled with the implantable component to deliver electrical power. In some embodiments, the wireless electrical power delivered to the implant may be amplitude modulated to provide communication from the external transceiver to the implant.

A shield 224 may separate the transceiver 226 from the inductive coil 222. In some embodiments, the shield 224 may be formed of a ferrous material. The shield 224 may be formed in a disk shape around an aperture in which the transceiver 228, lens 226, and lens cover 230 are disposed. In some embodiments, the shield 224 may be formed such that the inductive coil 222 may be received within the shield 224. The shield may be a ferrite designed to shape the electromagnetic field to increase the coupling between the external transceiver and the implanted device.

Figure 2C:
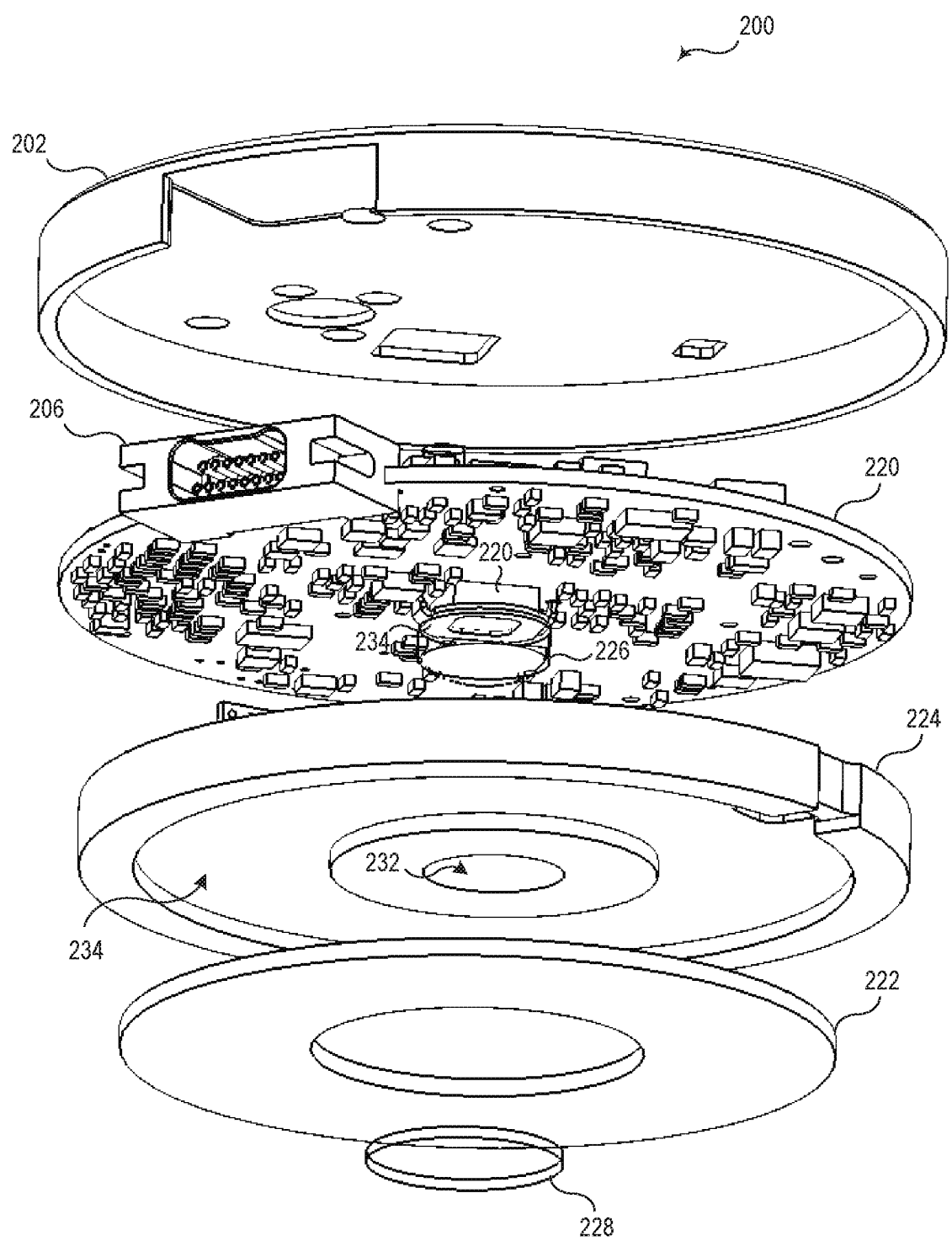
FIG. 2C illustrates a partially exploded view of the transceiver of FIG. 2A consistent with embodiments of the present disclosure.

FIG. 2C illustrates a partially exploded view of the external transceiver assembly of FIG. 2A consistent with embodiments of the present disclosure. The bottom portion of housing 202 is omitted to avoid obscuring details of the disclosure. The connector 206 and transceiver 228 are disposed on PCB 220.

Shield 224 is formed in a disk shape with an aperture 232 in the center. The aperture 232 may receive the lens 226. The lens cover 228 may close aperture 232 in the lower portion of the housing. A channel 234 is formed around the lower perimeter of the shield 224. The coil 222 may be received within the shield 224.

Figure 3:
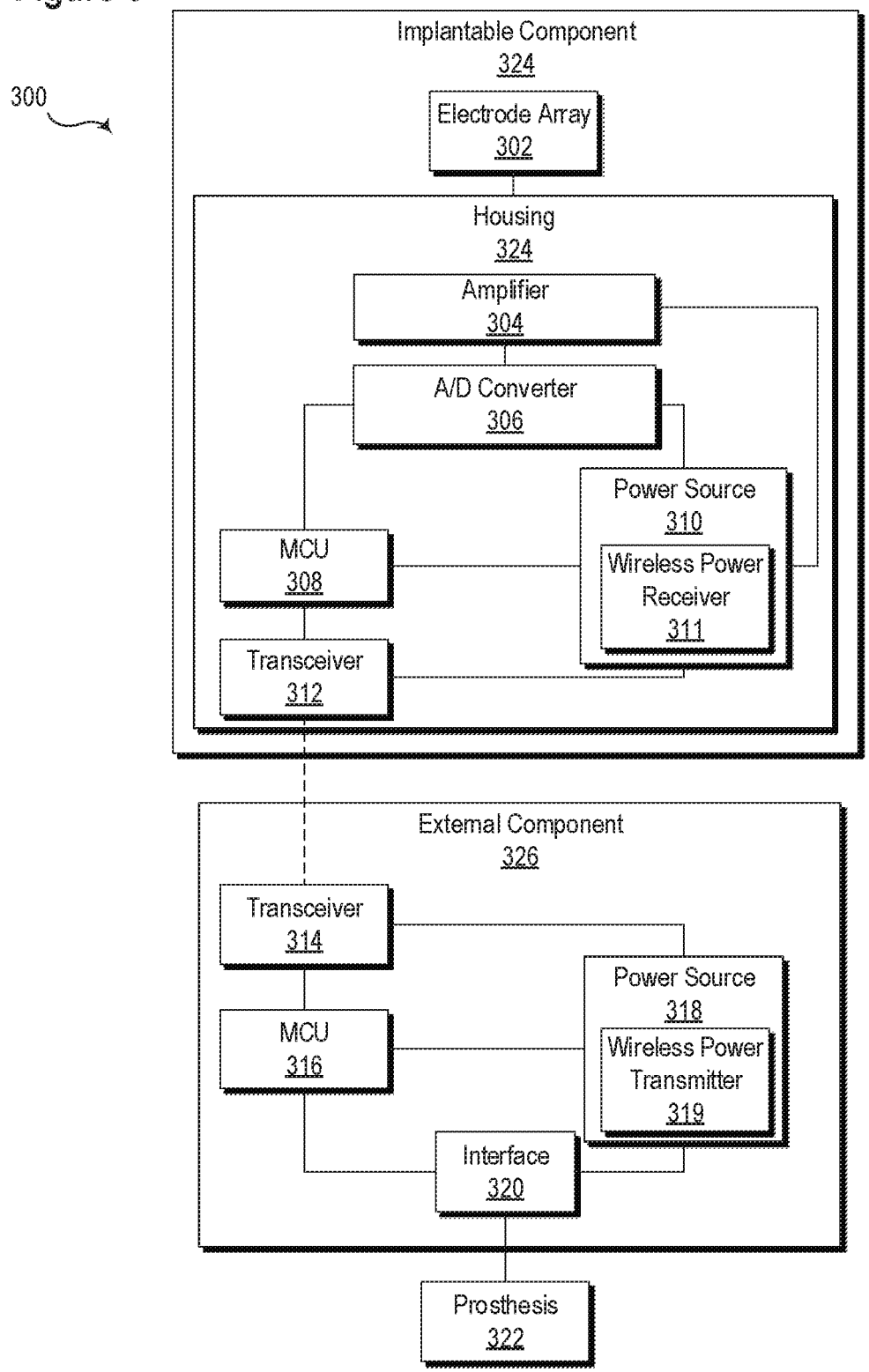
FIG. 3 illustrates a functional block diagram of an implantable sensor system consistent with embodiments of the present disclosure.

FIG. 3 illustrates a functional block diagram of an implantable sensor system 300 consistent with embodiments of the present disclosure. System 300 includes an electrode array 302, an implantable component 324, an external component 326, and a prosthesis 322 consistent with certain embodiments disclosed herein. According to various embodiments, electrode array 302 and/or housing 328 may be implanted. Housing 328 may have features designed to hold implanted structures in place, including but not limited to: screw points, suture holes, anchor points, and special films. Certain features may be reinforced by supplemental materials such as metal rings or polymer fibers to prevent tearing. The device may have terminal fixation points that may penetrate intramuscularly and be safely left in the body after explantation.

Implantable component 324, for example, may have electronics hermetically sealed in a small implantable enclosure. According to various embodiments, implantable component 324 may comprise an amplifier 304, which may be capable of multiple channels of bioamplification. Amplifier 304 may exhibit a relatively fast settle time to permit concurrent stimulation and recording with electrodes in close proximity.

Implantable component 324 may further comprise an ND converter 306 that is configured to convert the biopotential signals received from amplifier 304 to digital signals.

A microcontroller unit (MCU) 308 may perform signal processing operations and/or implement other functions. MCU 308 may comprise a microcontroller, microprocessor, programmable logic device, or any system used to perform signal processing and perform other functions described herein. Additional signal processing capabilities may be performed by external component 326. As illustrated in FIG. 3, external component 326 may also contain an MCU 316. Still further, additional processing may, according to some embodiments, be implemented using an external device 334 (e.g., a computer, a PDA, a tablet, a phone, or a remote control) connected via wireless communication interface 332. In one embodiment the wireless communication interface 332 may be embodied as a Bluetooth chipset.

Implantable component 324 may comprise an enclosure made of ceramic, metal, epoxy, polymeric material, or any combination thereof. Hermetic enclosures provide gas-tight areas that are created by metal, glass and ceramic enclosures, or epoxy. Implantable component 324 may include a hermetic enclosure to encapsulate portions of the implant components. Additional surgical materials, such as films, screws, etc., may be implanted to improve the tolerance, biocompatibility, or fixture of implantable component and/or health of skin or other tissues over or near implantable component 324. The device may include features such as tapers or edges to facilitate easier tunneling through tissue during surgical placement. Implantable component 324 may include non-stick or non-adhesive coatings on surfaces to make explantation easier.

In certain embodiments, electrode array 302 may be configured to extract biopotential signals from extramuscular and/or intramuscular sites. Electrode array 302 may, for example, be placed in the chest and/or shoulders, arms, hands, pelvic muscle, legs (upper and lower), or any other extramuscular or intramuscular site that may be used along with muscle decoding algorithms for control of prosthetic devices, computers, wheelchairs, robotic exoskeleton, and/or any other internal or external device.

A power source 310 may be located internally or externally to implantable component 324. Power source 310 may be embodied as an inductive device (i.e., an inductive coil for receiving power), such as wireless power receiver 311 or any other suitable system used for providing power to implantable component 324, or in some embodiments may include a battery and battery charging circuitry. In the illustrated embodiment, power may be provided inductively by the wireless power transmitter 319 in external component 326.

Transceiver 312 may communicate using a variety of technologies. In one embodiment, transceiver 314 may transmit signals by infrared transmission, reflected impedance transmission, amplitude modulation, and/or any applicable data transmission system. According to some embodiments, transmitted or received data may be recorded.

External component 326 may be in communication with prosthesis 322 via an interface 320. Signals received from electrode array 302 may be transmitted to prosthesis 322 to induce a desired action or movement. In some embodiments, external component 326 may be configured to be received within or integrated with prosthesis 322.

A power source 318 may comprise a wireless power transmitter 319 configured to transfer power to a wireless power receiver 311 associated with power source 310. In one specific embodiment, wireless power transmitter 319 may be embodied as an inductive coil 222, as illustrated in FIG. 2B. In some embodiments, power source 318 may receive power from prosthesis 322 via interface 320.

Figure 4:
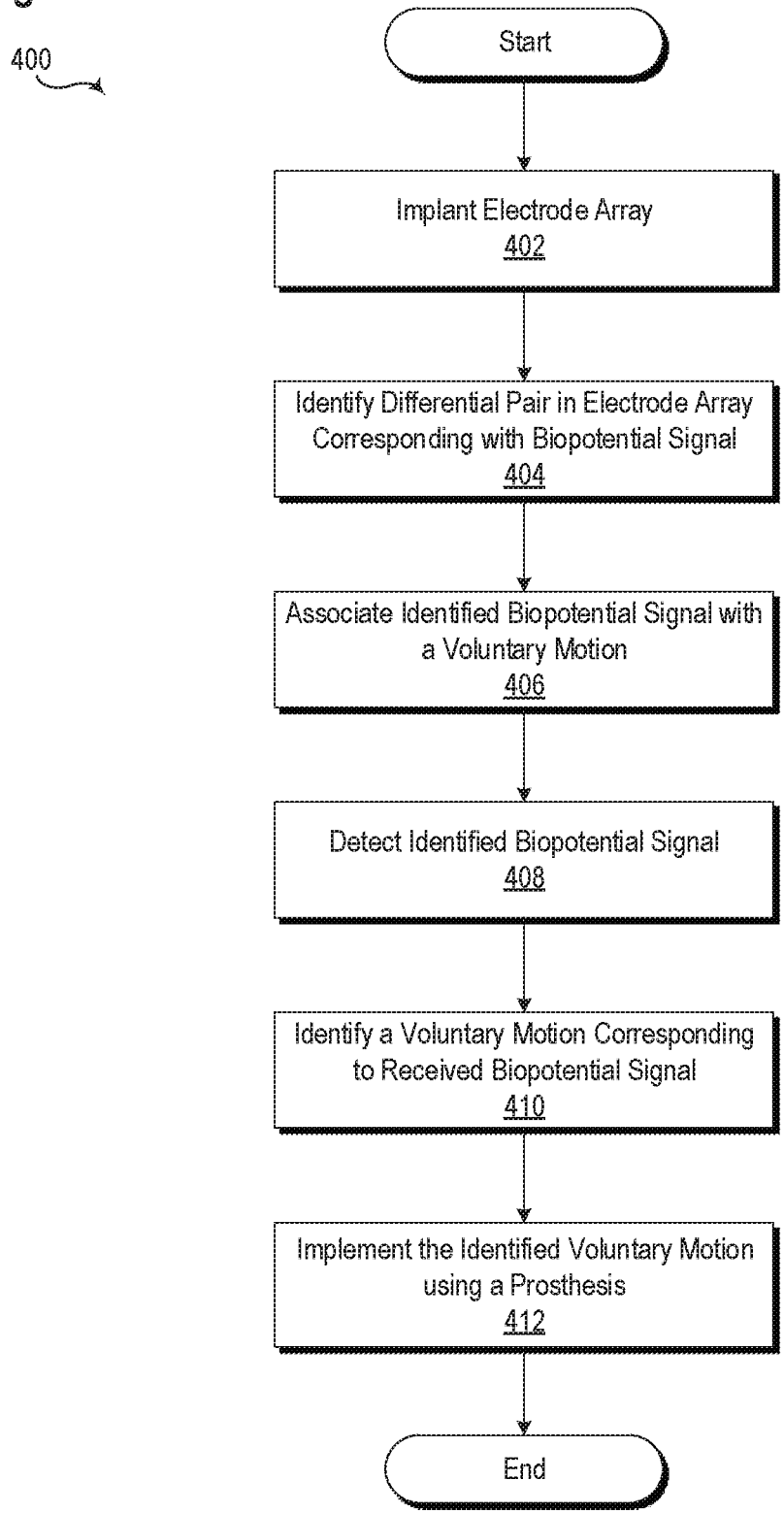
FIG. 4 illustrates a flow chart of a method of using an implantable myoelectric sensor system consistent with the present disclosure.

FIG. 4 illustrates an exemplary flow chart of a method 400 for controlling a prosthetic device using a system consistent with embodiments disclosed herein. At 402, an electrode array may be implanted. In one specific embodiment, the electrode array be comprised by the implantable component 100 illustrated in FIG. 1. In other embodiments, the electrode array may be configured in a variety of ways (e.g., in a grid configuration).

At 404, one or more "virtual pairs" in the electrode array corresponding with a biopotential signal may be identified. In various embodiments the processing of signals from various electrodes may analyze inputs from a plurality of electrodes in the electrode array and identify one or more "virtual pairs" with desirable characteristics (e.g., a high signal-to-noise ratio). As noted above, it may be difficult to place electrodes within living tissue and to acquire desired biopotential signals (i.e., the nerve impulses that cause muscle voluntary muscle contraction or the muscle activity itself). Accordingly, in various embodiments consistent with the present disclosure, an array comprising a plurality of electrodes may be implanted and later analyzed to identify the electrode signals or composite signals from two or more signals that are best situated for a particular task (e.g., use of a muscle group on a residual limb for control of a prosthesis).

At 406, an identified biopotential signal may be associated via signal processing with a voluntary motion. In some embodiments, a signal "virtual pair" signal may be associated with one or more actions. For example, an identified signal may be associated with a motion to grasp an object with a prosthetic hand. The motion of grasping an object may include a plurality of motions associated with each finger, in addition to positioning the thumb. In some embodiments, all the associated motions may be triggered.

A plurality of biopotential signals may be associated with a plurality of voluntary motions, and the biopotential signals may be detected using multiple "virtual pairs". In one example, a first signal associated with a grasping motion may be detected using a first "virtual pair" in the electrode array, and a second signal associated with a pointing motion may be detected using a second "virtual pair". In some embodiments, the actions at 402-406 may be associated with a commissioning or training, while the actions at 408-412 may be associated with use of the device. Such training or commissioning may allow for a plurality of motions to be associated with a plurality of biopotential signals.

Many changes may be made to the details of the above-described embodiments without departing from the underlying principles of the invention. The scope of the present invention should, therefore, be determined only by the following claims.

What is claimed is:
1. A sensor system, comprising:
an implantable component, comprising:
an electrode array disposed on a plurality of leads, each lead comprising a plurality of electrodes coupled to the implantable component and configured to receive a plurality of biopotential signals;
a housing, comprising:
a wireless power receiver configured to wirelessly receive electrical power;
an analog to digital converter configured to generate a plurality of digital representations of the biopotential signals;
a wireless data transmitter configured to transmit the plurality of digital representations of the biopotential signals; and
an external component, comprising:
a wireless data receiver configured to receive the plurality of digital representations of the biopotential signals;
a wireless power transmitter configured to wirelessly transmit electrical power to the implantable component;
a shielding component configured to shield the wireless data receiver from the wireless power transmitter; and
an interface configured to communicate with a prosthesis and configured to cause the prosthesis to implement a voluntary motion based on the plurality of digital representations of the biopotential signals;
wherein at least one of the plurality of sensing leads comprises a flexible lead that may be independently positioned within a muscle group with respect to at least one other of the plurality of leads.

2. The system of claim 1, wherein the wireless data transmitter comprises an infrared transmitter and the wireless data receiver comprises an infrared receiver.

3. The system of claim 1, wherein the wireless power transmitter and the wireless power receiver are configured to transfer power using inductive coupling.

4. The system of claim 1, wherein the shielding component comprises a recess configured to receive the wireless power transmitter.

5. The system of claim 3, wherein the shielding component comprises an aperture and the wireless data receiver is disposed in the aperture.

6. The system of claim 1, wherein the shielding component comprises a ferrous material.

7. The system of claim 1, wherein the external component is configured to receive power from the prosthesis.

8. The system of claim 1, wherein each of the plurality of biopotential signals comprise a representation of a difference between a reference electrode in the electrode array and any other electrode in the electrode array.

9. The system of claim 1 wherein two of the plurality of biopotential signals from two electrodes in the electrode array are combined to generate a virtual pair.

10. The system of claim 1, wherein the housing is hermetically sealed.

11. The system of claim 1, wherein the housing comprises a plurality of anchor points configured to anchor the housing to adjacent tissue.

12. The system of claim 1, wherein the plurality of biopotential signals comprise myoelectric signals.

13. The system of claim 1, wherein the shield is designed to shape the electromagnetic field of the power transmitter for better coupling and alignment tolerance between the external transceiver and the implantable component.

14. The system of claim 1, wherein a tuning element is accessible to a user to optimize the power transfer between the external transceiver and the implantable component.

15. The system of claim 1, further comprising a second electromagnetic shield disposed over the receiver to shield the receiver from noise from the power transmitter.

16. The system of claim 1, wherein the wireless power transmitter comprises a tunable element configured to adjust a power transfer efficiency.

17. A sensor system, comprising:
an implantable component, comprising:
an electrode array coupled to the implantable component and configured to receive a plurality of biopotential signals;
a housing, comprising:
a wireless power receiver configured to wirelessly receive electrical power;
an analog to digital converter configured to generate a plurality of digital representations of the biopotential signals; and
a wireless data transmitter configured to transmit the plurality of digital representations of the biopotential signals; and
an external component, comprising:
a wireless data receiver configured to receive the plurality of digital representations of the biopotential signals;
a lens disposed between the wireless data receiver and the wireless data transmitter and configured to focus a signal transmitted by the wireless data transmitter on the wireless data receiver;
a power source comprising a wireless power transmitter configured to wirelessly transmit electrical power to the implantable component;
a shielding component configured to shield the wireless data receiver from the wireless power transmitter; and
an interface configured to communicate with a prosthesis and configured to cause the prosthesis to implement a voluntary motion based on the plurality of digital representations of the biopotential signals.

18. A sensor system, comprising:
an implantable component, comprising:
an electrode array disposed on a plurality of leads, each lead comprising a plurality of electrodes coupled to the implantable component and configured to receive a plurality of biopotential signals, at least one of the plurality of leads comprising an anchor configured to oppose motion in the direction of a housing;
the housing, comprising:
a wireless power receiver configured to wirelessly receive electrical power;
an analog to digital converter configured to generate a plurality of digital representations of the biopotential signals; and
a wireless data transmitter configured to transmit the plurality of digital representations of the biopotential signals; and
an external component, comprising:
a wireless data receiver configured to receive the plurality of digital representations of the biopotential signals;
a wireless power transmitter configured to wirelessly transmit electrical power to the implantable component;
a shielding component configured to shield the wireless data receiver from the wireless power transmitter; and
an interface configured to communicate with a prosthesis and configured to cause the prosthesis to implement a voluntary motion based on the plurality of digital representations of the biopotential signals, wherein at least one of the plurality of sensing leads comprises a flexible lead that may be independently positioned within a muscle group with respect to at least one other of the plurality of leads.

* * * * *